United States Patent [19]
Peckham

[11] Patent Number: 5,143,062
[45] Date of Patent: Sep. 1, 1992

[54] ENDOTRACHEAL TUBE HAVING IRRIGATION MEANS

[75] Inventor: Keith A. Peckham, Neunkirchen-Seelscheid, Fed. Rep. of Germany

[73] Assignee: Mallinckrodt Medical, Inc., St. Louis, Mo.

[21] Appl. No.: 605,216

[22] Filed: Oct. 26, 1990

[51] Int. Cl.5 .............................................. A61M 16/04
[52] U.S. Cl. .......................... 128/207.14; 128/207.15; 604/43; 604/102
[58] Field of Search ...................... 128/207.14, 207.15, 128/200.26, 911, 912; 604/35, 102, 128, 43, 280, 281, 282

[56] References Cited

U.S. PATENT DOCUMENTS

| | | | |
|---|---|---|---|
| 550,238 | 11/1895 | Allen | 604/102 |
| 2,286,462 | 6/1942 | Chaffin | 604/43 |
| 4,156,428 | 5/1979 | Henkin | 128/207.15 |
| 4,305,392 | 12/1981 | Chester | 128/207.15 |
| 4,601,697 | 7/1986 | Mammolenti et al. | 604/43 |
| 4,632,108 | 12/1986 | Geil | 128/207.14 |
| 4,840,173 | 6/1989 | Porter, III | 128/207.14 |

Primary Examiner—Edgar S. Burr
Assistant Examiner—Stephen R. Funk
Attorney, Agent, or Firm—David A. Hey

[57] ABSTRACT

The present invention relates to an endotracheal tube used for mechanical ventilation of a hospital patient, the endotracheal tube is useful in evacuating contaminated secretions that pool within the trachea above an inflatable cuff associated with the endotracheal tube. The endotrocheal tube of the present invention comprises a double lumen through which air may be circulated, thus creating an indirect gentle suction through a suction eye communicating with the distal ends of the lumens, and located at a position proximal to the inflation cuff. This gentle indirect suction reduces the risk of damage to the tracheal mucosa, which often occurs when applying direct suction.

5 Claims, 1 Drawing Sheet

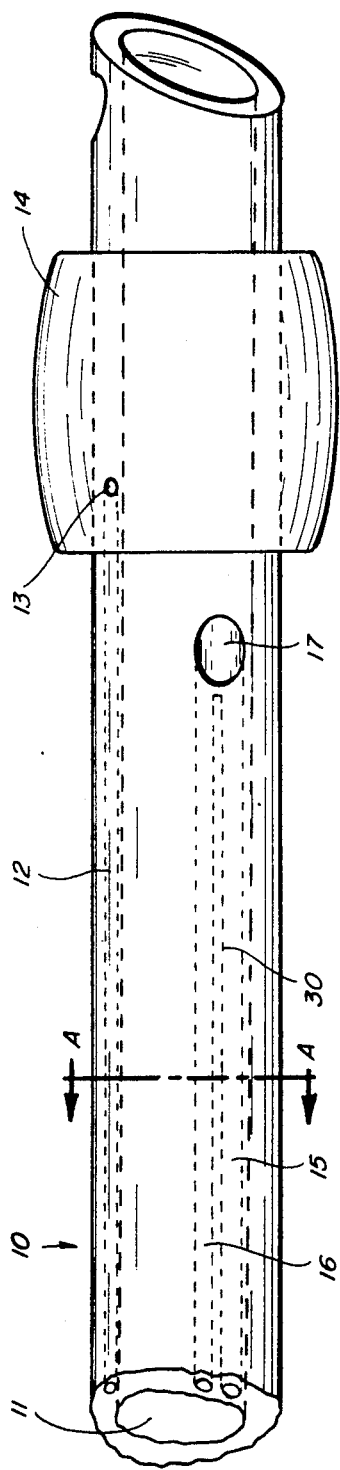
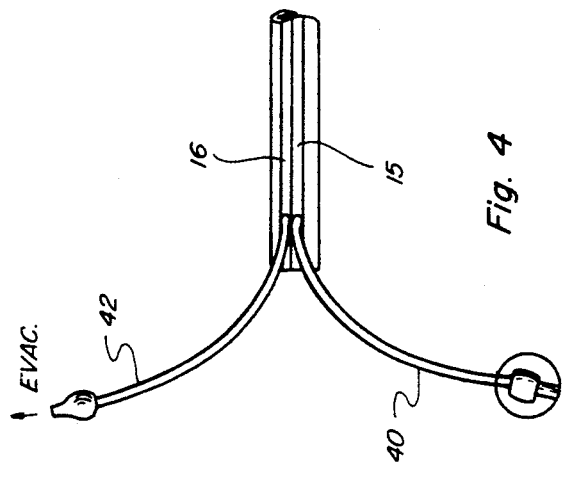
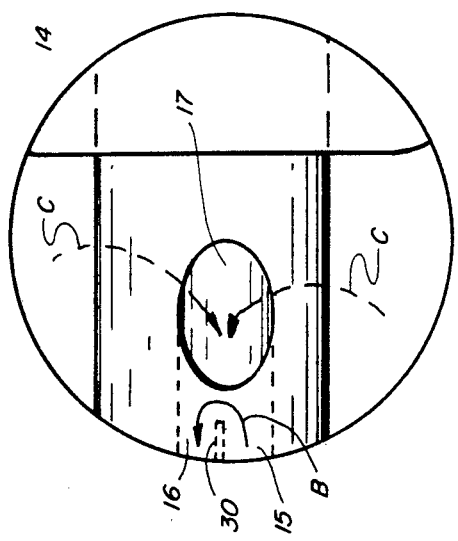
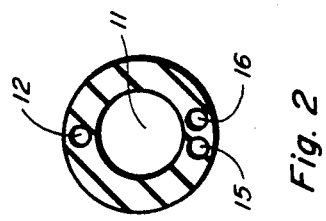

ENDOTRACHEAL TUBE HAVING IRRIGATION MEANS

BACKGROUND OF THE INVENTION

The present invention relates to an endotracheal tube used for mechanical ventilation of a hospital patient, by insertion of the tube into the trachea of the patient. In particular, the present invention relates to an endotracheal tube having means for irrigating and/or evacuating contaminated secretions accumulating above the tracheal tube cuff and thereby reducing the risk of such contaminated secretions entering the lungs of the patient.

Endotracheal intubation involves the insertion of a tubular device, known as an endotracheal tube, into the trachea of a patient. The endotracheal tube passes through the trachea and terminates at a position above the carina, anterior to a position between the second and fourth thoracic vertebrate. Gases may then be introduced through the endotracheal tube and into the lungs of the patient.

The primary purposes of endotracheal intubation, are to mechanically ventilate the patient's lungs, when a disease prevents the patient from normal, breathing induced ventilation, or to apply anesthetic gases during surgical intervention. In order to create enough air pressure to accomplish such mechanical ventilation and to prevent escape of gases past the tube, it is necessary to seal the passageway around the endotracheal tube. A seal may be produced by the use of an inflatable cuff formed integrally with and surrounding the endotracheal tube. When the endotracheal tube has been introduced into the patient's trachea, the inflatable cuff will normally be located about 3 to 5 centimeters above the carina and within the tube—like trachea.

The inflatable cuff is then inflated so as to engage the wall of the trachea and thereby seal the trachea and prevent gases being introduced through the tracheal tube from simply backing up around the tube. While treatment of this sort has proved successful for patients having chronic or acute respiratory diseases, there is a constant risk of several complications.

In particular, many patients receiving endotracheal intubation develop pneumonia, resulting from an infection of the lungs, possibly induced by contaminated, pooled secretions entering the trachea and the lungs after bypassing the epiglottis during intubation. The epiglottis normally operates as a valve which selectively closes the entry into the trachea and lungs, to prevent the introduction of secretions and particulate matter. However, when an endotracheal tube is in place, the epiglottis is held in an open position, and secretions which would normally be directed away from the trachea and into the digestive system, instead follow the path of the endotracheal tube and pool above the inflatable cuff of the endotracheal tube.

The greatest risk of such infectious secretions reaching the lungs is upon the cessation of mechanical ventilation. In particular, when the need for endotracheal intubation ends, the inflatable cuff of the endotracheal tube is deflated so that the endotracheal tube may be withdrawn from the patient. The infectious secretions which have pooled above the inflatable cuff are then released and are free to flow into the lungs, where bronchitis or pneumonia may rapidly develop. There is also the risk of the infectious secretions reaching the lungs during the intubation, by aspiration of the secretions past the tracheal tube cuff.

To overcome these risks, it is known in the prior art to combine a single lumen suction tube with an endotracheal tube. The suction tube is joined to the endotracheal tube in a suitable manner, the end of the suction tube terminating at a position above the inflatable cuff. The suction tube provides means for suction or evacuation of any pooled secretions which accumulate in the trachea above the inflatable cuff. However, such prior art devices have the disadvantage that use of a single lumen for the suction tube often causes direct suction to be exerted on the tracheal mucosa which may then result in damage to the mucosa.

U.S. Pat. No. 4,840,173 to Porter III, describes an endotracheal tube having a single lumen suction tube merged thereto. In particular, this patent describes a device wherein the suction tube is laminated to the outside of the ventilation tube, so that the suction tube terminates at a position just above the inflatable cuff. The suction tube includes multiple openings which may be used to evacuate secretions which pool above the inflatable cuff. In addition, the inflatable cuff includes a section immediately adjacent to the end of the suction tube that is less flexible than the rest of the inflatable cuff, to insure that the flexible material of the inflatable cuff is not sucked up against the suction tube openings. The endotracheal tube described in the Porter III patent has the disadvantages noted above, that the single lumen suction tube may exert suction on the tracheal mucosa and thereby cause damage to the mucosa. Further, the Porter III device is of a relatively complex design, requiring difficult processing, resulting in expensive production.

OBJECTS OF THE PRESENT INVENTION

It is one object of the present invention to provide an endotracheal tube having means for evacuation or suction of infectious secretions that may have pooled above the inflatable cuff of the endotracheal tube when the endotracheal tube is in place within a patient's trachea.

It is a further object of the present invention to provide an endotracheal tube as described above, which exerts a relatively gentle suction action, and avoids damage to the tracheal mucosa.

Further objects of the present invention will be evident from the following detailed description of the present invention.

SUMMARY OF THE PRESENT INVENTION

The objects of the present invention may be accomplished by providing an endotracheal tube having a double lumen sump action evacuating means associated therewith. In particular, the endotracheal tube according to the present invention includes a double lumen evacuating means, which is formed into the walls of the endotracheal tube, the evacuating means terminating at a suction eye positioned above an inflatable cuff for the endotracheal tube.

BRIEF DESCRIPTION OF THE DRAWINGS

FIG. 1 is a plan view showing details of the distal end of an endotracheal tube according to the present invention.

FIG. 2 is a cut away end view along the plane A—A of FIG. 1.

FIG. 3 is an expanded area view showing details of the suction eye of an endotracheal tube according to the present invention.

FIG. 4 is a plan view showing details of the proximal end of an endotracheal tube according to the present invention.

DETAILED DESCRIPTION OF THE PRESENT INVENTION

FIG. 1 shows an endotracheal tube 10, according to the present invention. The endotracheal tube 10, includes a main lumen 11, which extends the entire length of the endotracheal tube 10, and provides means to supply ventilating gases from an external source to a patient's lungs. The endotracheal tube 10, further includes a standard inflatable cuff 14, which may be inflated and deflated through a cuff lumen 12, formed in the wall of the endotracheal tube 10, and extending from the proximal end of the endotracheal tube 10, to an inflation opening 13, located within and opening into the interior of the inflatable cuff 14.

The endotracheal tube 10, according to the present invention, also includes double lumen evacuating means comprising a first lumen 15, and a second lumen 16. The first lumen 15, and second lumen 16, are also formed within the wall of the endotracheal tube 10, and extend parallel and in close proximity to each other, from the proximal end of the endotracheal tube 10, to a suction eye 17, located proximal to the inflatable cuff 14.

FIG. 2 is a cut away end view taken along the plane A—A in FIG. 1, and shows the arrangement of the various lumens of the endotracheal tube 10. In particular, the main lumen 11, extends through the middle of the endotracheal tube 10, while the cuff lumen 12, first lumen 15, and second lumen 16, are each formed into the walls of the endotracheal tube 10. In a preferred configuration, the cuff lumen 12, is formed to be on the opposite side of the endotracheal tube 10, from the first lumen 15, and second lumen 16.

FIG. 3 is an expanded area view showing details of the suction eye 17, of the endotracheal tube 10, according to the present invention. In particular, as shown in FIG. 3, the first lumen 15, and the second lumen 16, are separated by a separation wall 30, which extends from the proximal end of the endotracheal tube 10, to a position slightly proximal to the suction eye 17. In a preferred embodiment, the separation wall 30, terminates at a position approximately 5 mm proximal to the beginning of the suction eye 17, in order to avoid direct suction on the tracheal wall. By virtue of the separation wall 30, the first lumen 15, and the second lumen 16, are separated along the majority of their lengths and are joined only at their distal ends, at a position corresponding to the location of the suction eye 17.

FIG. 4 shows the details of the proximal end of the endotracheal tube 10, which includes connection adapters for operating the double lumen evacuation means. In particular, a sump or lavage connector 40, is attached to the first lumen 15, while an evacuation connector 42, is attached to the second lumen 16. Also, a standard inflation connector (not shown) is attached to the cuff lumen 12. The sump connector 40, and evacuation connector 42, act in unison to operate the double lumen evacuating means of the endotracheal tube 10, as will be fully explained below.

In operation, the endotracheal tube 10, is inserted into the patient's trachea using standard endotracheal intubation techniques. Once the endotracheal tube 10, is properly located, the inflatable cuff 14, is inflated by supplying inflation medium through the cuff lumen 12, until the inflatable cuff 14, adequately seals the trachea. Mechanical ventilation of the patient's lungs may then be carried out using standard operating procedures. During the intubation, secretions that pool in the trachea above the inflatable cuff 14, may be evacuated using the double lumen evacuating means of the present invention in the following manner. Air is supplied through the sump connector 40, while a vacuum is applied to the evacuation connector 42. In this manner, air circulates through the double lumen evacuating means, by passing down the first lumen 15, around the distal end of the separation wall 30, and then up the second lumen 16. (See arrow B in FIG. 3). This circulation through the first lumen 15, and second lumen 16, causes a gentle suction action to be applied through the suction eye 17, which suction may be used to evacuate any pooled secretions from around the inflatable cuff 14, through the second lumen 16, and out the evacuation connector 42. (See arrows C in FIG. 3). Direct suction on the tracheal wall is avoided by terminating the separation wall 30, at a position slightly proximal to the beginning of the suction eye 17. The amount and strength of suction may be easily controlled by controlling the amount of air supplied through the sump connector 40, and the degree of vacuum applied to the evacuation connector 42. When the need for mechanical ventilation no longer exists, the inflatable cuff 14, may be deflated, without risk of infectious secretions flowing into the lungs of the patient, and the endotracheal tube 10, may be removed using standard intubation procedures.

The endotracheal tube 10, according to the present invention provides several advantages over the endotracheal tubes known in the prior art. In particular, the double lumen evacuating means allows secretions which pool in the trachea around the inflatable cuff 14, to be evacuated quickly and easily, thereby reducing the risk of infection to the lungs of the patient.

Further, the endotracheal tube 10, according to the present invention has the advantage over prior art endotracheal tubes having single lumen evacuating means, that the suction applied through the double lumen evacuating means of the present invention, avoids damage to the tracheal mucosa. In other words, the suction applied through the suction eye 17, is indirect; i.e. is caused by the circulation of air through the first lumen 15, and the second lumen 16; and therefore, the risk of damage to the tracheal mucosa is greatly reduced. This indirect suction is particularly made possible by terminating the separation wall 30, between the first lumen 15, and the second lumen 16, at a position slightly proximal to the beginning of the suction eye 17.

Moreover, by forming the cuff lumen 12, the first lumen 15, and the second lumen 16, into the walls of the endotracheal tube 10, production may be made easier and less costly, and the final product may be made more sturdy and reliable.

In addition, the double lumen evacuating means of the present invention may be used to sterilize the area of accumulation of pooled secretions, by cycling of a medicated solution. In this alternative, medicated solution may be supplied through the first lumen 15, while no vacuum is applied to the evacuation connector 42, thereby allowing the medicated solution to pass out of the suction eye 17 The medicated solution then creates its own pool within the trachea where it may mix with infectious secretions, and act to neutralize the bacteria within such secretions. When it becomes necessary to replenish medicated solution, the entire mixed pool may be evacuated by operation of the double lumen evacuating means as previously described. This same process may also be used to treat other problems that may occur within the trachea, such as inflammation caused by the presence of the endotracheal tube.

The foregoing has been a description of certain preferred embodiments of the present invention, but is not intended to limit the invention in any way. Rather, many modifications, variations and changes in detail may be made within the scope of the present invention.

What is claimed is:

1. An endotracheal tube for insertion into the trachea of a patient, to enable mechanical ventilation of the lungs of the patient, said endotracheal tube comprising:
    a main body comprising a tube having a wall surrounding and defining a single lumen tube, said main body comprising means to supply ventilating gases from an external source to the lungs of the patient and said main body having a proximal end and a distal end;
    an inflatable cuff sealed to and surrounding said main body, at a location near the distal end of said main body, such that when said endotracheal tube is properly located within the patient, said inflatable cuff may be inflated to seal the trachea of the patient;
    means to inflate and deflate said inflatable cuff; and
    double lumen evacuating means for irrigation and/or for suction removal of secretions which may pool in the trachea around the endotracheal tube and above the inflatable cuff;
    wherein said double lumen evacuating means comprises a first lumen and a second lumen formed within said wall of said main body, and extending parallel and in close proximity to each other, from the proximal end of said main body to a suction eye formed through a portion of said wall of said main body, said suction eye being located proximal to said inflatable cuff;
    wherein said first lumen and said second lumen are separated by a separation wall along the majority of their lengths, from the proximal end of said main body to a position proximal to the beginning of said suction eye, such that said first lumen and said second lumen are connected at a position corresponding approximately to the location of said suction eye.

2. An endotracheal tube according to claim 1, wherein said separation wall extends from the proximal end of said main body to a position approximately 5 mm proximal to the beginning of said suction eye.

3. An endotracheal tube according to claim 1, wherein said means to inflate and deflate said inflatable cuff comprises a cuff lumen formed within said wall of said main body, and extending from the proximal end of said main body, to an inflation opening formed through a portion of said wall of said main body, said inflation opening communicating with the interior of said inflatable cuff.

4. An endotracheal tube according to claim 1, wherein the proximal end of said main body includes a connector for connecting operating means for operation of said double lumen evacuating means.

5. An endotracheal tube according to claim 4, wherein said operating means includes a sump or lavage connector attached to said first lumen, and an evacuation connector attached to said second lumen.

* * * * *